United States Patent
Derakhshan et al.

(10) Patent No.: US 11,850,111 B2
(45) Date of Patent: Dec. 26, 2023

(54) COMPARATIVE ORTHODONTIC TREATMENT PLANNING TOOL

(71) Applicant: Align Technology, Inc., San Jose, CA (US)

(72) Inventors: Mitra Derakhshan, Herndon, VA (US); Angelo Maura, Amsterdam (NL)

(73) Assignee: Align Technology, Inc., San Jose, CA (US)

( * ) Notice: Subject to any disclaimer, the term of this patent is extended or adjusted under 35 U.S.C. 154(b) by 453 days.

(21) Appl. No.: 14/695,921

(22) Filed: Apr. 24, 2015

(65) Prior Publication Data

US 2016/0310235 A1 Oct. 27, 2016

(51) Int. Cl.
*A61C 7/00* (2006.01)
*A61C 7/08* (2006.01)
*G16H 50/50* (2018.01)

(52) U.S. Cl.
CPC ............... *A61C 7/002* (2013.01); *A61C 7/08* (2013.01); *G16H 50/50* (2018.01)

(58) Field of Classification Search
CPC ........... A61C 7/00; A61C 7/002; A61C 7/146; A61C 13/0004; A61C 7/08; G06F 19/321; G16H 20/40; G16H 50/50; G06Q 10/0637
USPC ............................................ 433/24; 705/3, 7
See application file for complete search history.

(56) References Cited

U.S. PATENT DOCUMENTS

| | | | |
|---|---|---|---|
| 2,467,432 A | 4/1949 | Kesling | |
| 3,407,500 A | 10/1968 | Kesling | |
| 3,600,808 A | 8/1971 | Reeve | |
| 3,660,900 A | 5/1972 | Andrews | |
| 3,683,502 A | 8/1972 | Wallshein | |
| 3,738,005 A | 6/1973 | Cohen et al. | |
| 3,860,803 A | 1/1975 | Levine | |
| 3,916,526 A | 11/1975 | Schudy | |
| 3,922,786 A | 12/1975 | Lavin | |
| 3,950,851 A | 4/1976 | Bergersen | |
| 3,983,628 A | 10/1976 | Acevedo | |
| 4,014,096 A | 3/1977 | Dellinger | |
| 4,195,046 A | 3/1980 | Kesling | |

(Continued)

FOREIGN PATENT DOCUMENTS

| | | | |
|---|---|---|---|
| AU | 3031677 A | 5/1979 | |
| AU | 517102 B2 | 7/1981 | |

(Continued)

OTHER PUBLICATIONS

U.S. Appl. No. 13/186,374, filed Jul. 19, 2011.

(Continued)

*Primary Examiner* — Edward Moran
*Assistant Examiner* — Matthew P Saunders
(74) *Attorney, Agent, or Firm* — FORTEM IP LLP

(57) ABSTRACT

A comparative orthodontic treatment planning tool that can provide multiple treatment plan options based on a single initial tooth data set. A user can use the treatment planning tool to select a treatment plan based on factors, including cost, treatment duration, treatment complexity, and material or feature selection. Tooth arrangements at different treatment stages can be compared. In some cases, a tooth arrangement at one treatment stage can be superimposed over a tooth arrangement at a different treatment stage or over a tooth arrangement from a different treatment plan.

20 Claims, 10 Drawing Sheets

(56) References Cited

U.S. PATENT DOCUMENTS

| | | |
|---|---|---|
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,882,192 A * | 3/1999 | Bergersen ............... A61C 7/00 433/2 |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A * | 11/1999 | Chishti ................... A61C 7/00 433/24 |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,450,807 B1 | 9/2002 | Chishti et al. |
| 6,482,298 B1 | 11/2002 | Bhatnagar |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 7,077,647 B2 * | 7/2006 | Choi ...................... A61C 7/00 433/213 |
| 7,107,226 B1 * | 9/2006 | Cassidy ............ G06Q 30/0625 705/26.62 |
| 7,156,655 B2 * | 1/2007 | Sachdeva ............... A61C 7/00 433/213 |
| 7,156,661 B2 | 1/2007 | Choi et al. |
| 7,717,708 B2 * | 5/2010 | Sachdeva ............... A61C 7/00 433/24 |
| 7,870,280 B2 | 1/2011 | Kuo |
| 7,880,751 B2 | 2/2011 | Kuo et al. |
| 7,930,189 B2 | 4/2011 | Kuo |

(56) References Cited

U.S. PATENT DOCUMENTS

| | | | |
|---|---|---|---|
| 7,970,627 B2 | 6/2011 | Kuo et al. | |
| 7,970,628 B2 | 6/2011 | Kuo et al. | |
| 8,075,306 B2* | 12/2011 | Kitching | A61C 7/00 382/128 |
| 8,740,614 B2* | 6/2014 | Wen | A61C 7/00 433/24 |
| 8,790,118 B2* | 7/2014 | Lehmann | A61C 13/0004 433/223 |
| 8,843,381 B2 | 9/2014 | Kuo et al. | |
| 8,874,452 B2 | 10/2014 | Kuo | |
| 9,108,338 B2 | 8/2015 | Sirovskiy et al. | |
| 10,548,690 B2* | 2/2020 | Wen | G16H 30/20 |
| 2002/0006597 A1 | 1/2002 | Andreiko et al. | |
| 2002/0064746 A1* | 5/2002 | Muhammad | A61C 7/00 433/24 |
| 2002/0187451 A1* | 12/2002 | Phan | A61C 7/00 433/6 |
| 2002/0188478 A1* | 12/2002 | Breeland | G16H 10/60 705/3 |
| 2003/0009252 A1 | 1/2003 | Pavlovskaia et al. | |
| 2003/0027098 A1* | 2/2003 | Manemann | G16H 30/40 433/24 |
| 2003/0139834 A1 | 7/2003 | Nikolskiy et al. | |
| 2003/0224311 A1 | 12/2003 | Cronauer | |
| 2004/0128010 A1 | 7/2004 | Pavlovskaia et al. | |
| 2004/0197727 A1 | 10/2004 | Sachdeva et al. | |
| 2005/0010450 A1* | 1/2005 | Hultgren | A61C 13/0004 705/3 |
| 2005/0055118 A1 | 3/2005 | Nikolskiy et al. | |
| 2005/0191594 A1* | 9/2005 | Taub | A61C 7/00 433/24 |
| 2005/0271996 A1* | 12/2005 | Sporbert | A61C 7/00 433/24 |
| 2006/0064329 A1* | 3/2006 | Abolfathi | B33Y 80/00 705/3 |
| 2006/0275731 A1* | 12/2006 | Wen | A61C 7/00 433/24 |
| 2006/0275736 A1* | 12/2006 | Wen | A61C 9/00 433/213 |
| 2007/0128573 A1* | 6/2007 | Kuo | A61C 7/08 433/24 |
| 2008/0305452 A1* | 12/2008 | Sterental | A61C 7/08 433/24 |
| 2008/0305454 A1* | 12/2008 | Kitching | A61C 7/00 433/24 |
| 2009/0087046 A1* | 4/2009 | Kuhn | A61B 5/00 382/128 |
| 2010/0167225 A1 | 7/2010 | Kuo | |
| 2011/0159451 A1* | 6/2011 | Kuo | G06F 30/00 433/24 |
| 2011/0270588 A1 | 11/2011 | Kuo et al. | |
| 2013/0231899 A1* | 9/2013 | Khardekar | G06F 30/00 703/1 |
| 2014/0379356 A1* | 12/2014 | Sachdeva | A61C 7/002 705/2 |
| 2016/0135925 A1* | 5/2016 | Mason | A61C 7/002 703/2 |
| 2020/0306011 A1* | 10/2020 | Chekhonin | G16H 50/50 |

FOREIGN PATENT DOCUMENTS

| | | | |
|---|---|---|---|
| AU | 5598894 A | 6/1994 | |
| CA | 1121955 A | 4/1982 | |
| CA | WO 2006050452 A2 * | 5/2006 | A61C 9/002 |
| CN | 101420920 A | 4/2009 | |
| CN | 101427256 A | 5/2009 | |
| CN | 101616637 | 12/2009 | |
| CN | 101616637 A | 12/2009 | |
| CN | 101969877 A | 2/2011 | |
| CN | 102245121 A | 11/2011 | |
| CN | 107212937 A | 9/2017 | |
| DE | 2749802 A1 | 5/1978 | |
| DE | 69327661 T2 | 7/2000 | |
| EP | 0091876 A1 | 10/1983 | |
| EP | 0299490 A2 | 1/1989 | |
| EP | 0376873 A2 | 7/1990 | |
| EP | 0490848 A2 | 6/1992 | |
| EP | 0541500 A1 | 5/1993 | |
| EP | 0667753 B1 | 1/2000 | |
| EP | 0774933 B1 | 12/2000 | |
| EP | 0731673 B1 | 5/2001 | |
| EP | 1609435 | 12/2005 | |
| EP | 1609435 A1 | 12/2005 | |
| ES | 463897 A1 | 1/1980 | |
| FR | 2369828 A1 | 6/1978 | |
| FR | 2652256 A1 | 3/1991 | |
| GB | 1550777 A | 8/1979 | |
| JP | S5358191 A | 5/1978 | |
| JP | H0428359 A | 1/1992 | |
| JP | H08508174 A | 9/1996 | |
| WO | WO-9008512 A1 | 8/1990 | |
| WO | WO-9104713 A1 | 4/1991 | |
| WO | WO-9410935 A1 | 5/1994 | |
| WO | WO-9832394 A1 | 7/1998 | |
| WO | WO-9844865 A1 | 10/1998 | |
| WO | WO-9858596 A1 | 12/1998 | |
| WO | 2006/118771 | 11/2006 | |
| WO | WO 2006118771 A2 * | 11/2006 | |

OTHER PUBLICATIONS

International Search Report dated Jul. 13, 2016, from International Application No. PCT/IB2016/000532.

Written Opinion dated Jul. 13, 2016 from International Application No. PCT/IB2016/000532.

AADR. American Association for Dental Research, Summary of Activities, Mar. 20-23, 1980, Los Angeles, CA, p. 195.

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

(56) References Cited

OTHER PUBLICATIONS

Baumrind, "Integrated Three-Dimensional Craniofacial Mapping: Background, Principles, and Perspectives," Semin. in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff, "Computerized Diagnostic Setups and Simulations," Angle Orthod., 40(1):28-36 (Jan. 1970).
Biggerstaff et al., "Computerized Analysis of Occlusion in the Postcanine Dentition," Am. J. Orthod., 61(3): 245-254 (Mar. 1972).
BIOSTAR Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004.
Bourke, "Coordinate System Transformation," (Jun. 1996), p. 1, retrieved from the Internet Nov. 5, 2004, URL< http://astronomy.swin.edu.au/-pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Burstone (interview), "Dr. Charles J. Burstone on The Uses of the Computer in Orthodontic Practice (Part 1)," J. Clin. Orthod., 13(7):442-453 (Jul. 1979).
Burstone (interview), "Dr. Charles J. Burstone on The Uses of the Computer in Orthodontic Practice (Part 2)," J. Clin. Orthod., 13(8):539-551 (Aug. 1979).
Cardinal Industrial Finishes, Powder Coatings information posted at< http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside, Part 2 F. Duret—A Man with a Vision, Part 3 The Computer Gives New Vision—Literally, Part 4 Bytes 'N Bites—The Computer Moves from the Front Desk to the Operatory," Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
DENT-X posted on Sep. 24, 98 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al., "CAD/CAM Imaging in Dentistry," Curr. Opin. Dent., 1:150-154 (1991).
Duret et al., "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet:< http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
GIM-ALLDENT Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates In Orthodontics and Orthognathic Surgery," JCO, pp. 262-328 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of

(56) References Cited

OTHER PUBLICATIONS

Japan KA Orthodontic Society, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," (Article Summary in English, article in German), Informatbnen, pp. 375-396 (Mar. 1991).

Hojjatie et al., "Three-Dimensional Finite Element Analysis of Glass-Ceramic Dental Crowns," J. Biomech., 23(11):1157-1166 (1990).

Huckins, "CAD-CAM Generated Mandibular Model Prototype from MRI Data," AAOMS, p. 96 (1999).

Important Tip About Wearing the Red White & Blue Active Clear Retainer System, Allesee Orthodontic Appliances—Pro Lab, 1 page 1998).

JCO Interviews, Craig Andreiko, DDS, MS on the Elan and Orthos Systems, JCO, pp. 459-468 (Aug. 1994).

JCO Interviews, Dr. Homer W. Phillips on Computers in Orthodontic Practice, Part 2, JCO. 1997; 1983:819-831.

Jerrold, "The Problem, Electronic Data Transmission and the Law," AJO-DO, pp. 478-479 (Apr. 1988).

Jones et al., "An Assessment of the Fit of a Parabolic Curve to Pre- and Post-Treatment Dental Arches," Br. J. Orthod., 16:85-93 (1989).

JP Faber et al., "Computerized Interactive Orthodontic Treatment Planning," Am. J. Orthod., 73(1):36-46 (Jan. 1978).

Kamada et.al., Case Reports On Tooth Positioners Using LTV Vinyl Silicone Rubber, J. Nihon University School of Dentistry (1984) 26(1): 11-29.

Kamada et.al., Construction of Tooth Positioners with LTV Vinyl Silicone Rubber and Some Case KJ Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling, Coordinating the Predetermined Pattern and Tooth Positioner with Conventional Treatment, KN Am. J. Orthod. Oral Surg. (1946) 32:285-293.

Kesling et al., The Philosophy of the Tooth Positioning Appliance, American Journal of Orthodontics and Oral surgery. 1945; 31:297-304.

Kleeman et al., The Speed Positioner, J. Clin. Orthod. (1996) 30:673-680.

Kochanek, "Interpolating Splines with Local Tension, Continuity and Bias Control," Computer Graphics, ri 18(3):33-41 (Jul. 1984). KM Oral Surgery (1945) 31 :297-30.

Kunii et al., "Articulation Simulation for an Intelligent Dental Care System," Displays 15:181-188 (1994).

Kuroda et al., Three-Dimensional Dental Cast Analyzing System Using Laser Scanning, Am. J. Orthod. Dentofac. Orthop. (1996) 110:365-369.

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).

Leinfelder, et al., "A New Method for Generating Ceramic Restorations: a CAD-CAM System," J. Am. 1-1 Dent. Assoc., 118(6):703-707 (Jun. 1989).

Manetti, et al., "Computer-Aided Cefalometry and New Mechanics in Orthodontics," (Article Summary in English, article in German), Fortschr Kieferorthop. 44, 370-376 (Nr. 5), 1983.

Mccann, "Inside the ADA," J. Amer. Dent. Assoc., 118:286-294 (Mar. 1989).

Mcnamara et al., "Invisible Retainers," J. Cfin. Orthod., pp. 570-578 (Aug. 1985).

Mcnamara et al., Orthodontic and Orthopedic Treatment in the Mixed Dentition, Needham Press, pp. 347-353 (Jan. 1993).

Moermann et al., "Computer Machined Adhesive Porcelain Inlays: Margin Adaptation after Fatigue Stress," IADR Abstract 339, J. Dent. Res., 66(a):763 (1987).

Moles, "Correcting Mild Malalignments—As Easy As One, Two, Three," AOA/Pro Corner, vol. 11, No. 1, 2 pages (2002).

Mormann et al., "Marginale Adaptation von adhasuven Porzellaninlays in vitro," Separatdruck aus: Schweiz. Mschr. Zahnmed. 95: 1118-1129, 1985.

Nahoum, "The Vacuum Formed Dental Contour Appliance," N. Y. State Dent. J., 30(9):385-390 (Nov. 1964).

Nash, "CEREC CAD/CAM Inlays: Aesthetics and Durability in a Single Appointment," Dent. Today, 9(8):20, 22-23 (Oct. 1990).

Nishiyama et al., "A New Construction of Tooth Repositioner by LTV Vinyl Silicone Rubber," J. Nihon Univ. Sch. Dent., 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Pinkham, "Foolish Concept Propels Technology," Dentist, 3 pages total, Jan./Feb. 1989.

Pinkham, "Inventor's CAD/CAM May Transform Dentistry," Dentist, 3 pages total, Sep. 1990.

Ponitz, "Invisible Retainers," Am. J. Orthod., 59(3):266-272 (Mar. 1971).

PROCERA Research Projects, "PROCERA Research Projects 1993—Abstract Collection," pp. 3-7; 28 (1993).

Proffit et al., Contemporary Orthodontics, (Second Ed.), Chapter 15, Mosby Inc., pp. 470-533 (Oct. 1993.

Raintree Essix & ARS Materials, Inc., Raintree Essix, Technical Magazine Table of contents and Essix Appliances,< http:// www.essix.com/magazine/defaulthtml> Aug. 13, 1997.

Redmond et al., "Clinical Implications of Digital Orthodontics," Am. J. Orthod. Dentofacial Orthop., 117(2):240-242 (2000).

Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).

Rekow, "CAD/CAM in Dentistry: A Historical Perspective and View of the Future," J. Can. Dent. Assoc., 58(4):283, 287-288 (Apr. 1992).

Rekow, "Computer-Aided Design and Manufacturing in Dentistry: A Review of the State of the Art," J. Prosthet. Dent., 58(4):512-516 (Oct. 1987).

Rekow, "Dental CAD-CAM Systems: What is the State of the Art?", J. Amer. Dent. Assoc., 122:43-48 1991.

Rekow et al., "CAD/CAM for Dental Restorations—Some of the Curious Challenges," IEEE Trans. Biomed. Eng., 38(4):314-318 (Apr. 1991).

Rekow et al., "Comparison of Three Data Acquisition Techniques for 3-D Tooth Surface Mapping," Annual International Conference of the IEEE Engineering in Medicine and Biology Society, 13(1):344-345 1991.

Rekow, "Feasibility of an Automated System for Production of Dental Restorations, Ph.D. Thesis," Univ. of Minnesota, 244 pages total, Nov. 1988.

Richmond et al., "The Development of a 3D Cast Analysis System," Br. J. Orthod., 13(1):53-54 (Jan. 1986).

Richmond et al., "The Development of the PAR Index (Peer Assessment Rating): Reliability and Validity," Eur. J. Orthod., 14:125-139 (1992).

Richmond, "Recording The Dental Cast In Three Dimensions," Am. J. Orthod. Dentofacial Orthop., 92(3):199-206 (Sep. 1987).

Rudge, "Dental Arch Analysis: Arch Form, A Review of the Literature," Eur. J. Orthod., 3(4):279-284 1981.

Sakuda et al., "Integrated Information-Processing System In Clinical Orthodontics: An Approach with Use of a Computer Network System," Am. J. Orthod. Dentofacial Orthop., 101(3): 210-220 (Mar. 1992).

Schellhas et al., "Three-Dimensional Computed Tomography in Maxillofacial Surgical Planning," Arch. Otolamp!. Head Neck Sur9., 114:438-442 (Apr. 1988).

(56) References Cited

OTHER PUBLICATIONS

Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the minipositioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utilisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances—Pro Lab product information for patients,< http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering Of Geometric Models—An Introduction," Computer-Aided Design, 29(4):255-268,1997.

Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987.
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be A Candidate For This Invisible No-Braces Treatment, Allesee Orthodontic Appliances—Pro Lab product information for patients, 2 pages (2002).

* cited by examiner

FIG. 6

COMPARATIVE ORTHODONTIC TREATMENT PLANNING TOOL

BACKGROUND OF THE INVENTION

The present invention relates generally to the field of orthodontics. More particularly, the invention relates to systems and methods of comparative orthodontic treatment planning.

A primary objective of orthodontics is to realign patients' teeth to positions where the teeth function optimally and have an aesthetically pleasing appearance. The goal of a doctor is to take the patient from his or her current condition ("initial arrangement") to a treatment goal ("final arrangement"). There may be many different ways to achieve the goal and these are known as "treatment options." The methodologies used by the doctor to help the patient reach the goal are known as "treatment plans."

Typically, appliances such as fixed braces and wires are applied to a patient's teeth to gradually reposition them from an initial arrangement to a final arrangement. As noted above, braces (wires and brackets) have been used for several decades to straighten and maintain tooth positioning. Over time and with a series of clinical visits and adjustments to the braces, the orthodontist adjusts the wires and brackets to move the teeth to their final position. However, as wires and brackets can be unsightly, uncomfortable, and cumbersome for the patient, removable polymeric shell appliances (e.g., aligners) were developed to straighten teeth. Clear aligners, such as the Invisalign® aligners manufactured by Align Technology, Inc. of San Jose, Calif., are virtually invisible as well as more convenient. Unlike patients with braces, the patient wearing aligners has the freedom to eat anything he or she desires because the aligners are removable. Furthermore, removable aligners allow for easier care and cleaning of teeth.

The Invisalign® System includes designing and/or fabricating multiple, and usually all, of the aligners to be worn by the patient before the aligners are administered to the patient and used to reposition the teeth (i.e., at the outset of treatment). Often, designing and planning a customized treatment for a patient includes using computer-based three-dimensional planning and design tools, such as ClinCheck® from Align Technology, Inc. The design of the aligners can rely on computer modeling of a series of planned successive tooth arrangements, and the individual aligners are designed to be worn over the teeth and elastically reposition the teeth to each of the planned tooth arrangements.

Typically, the treatment plan is based on one prescription form, which is based on one input and provides one output. However, different clinicians may vary in their definitions of individual orthodontic parameters and their view of how a case should ideally be treated will also often vary. Patients may also have different goals as well as different budgets. As a set of aligners is typically made prior to starting treatment, there is a need for a robust comparative treatment planning tool that allows both patients and doctors to view different options when making treatment planning decisions. In view of the foregoing, it would be desirable to have methods and systems to provide an interactive and dynamic orthodontic treatment planning tool.

SUMMARY OF THE INVENTION

In accordance with an embodiment, a method is provided for orthodontic treatment planning with a comparative orthodontic treatment planning tool. Initial tooth data set comprising an initial tooth arrangement is received at the treatment planning tool. The initial tooth data set is used to generate at least one treatment plan to move teeth from the initial arrangement. Each treatment plan comprises a plurality of treatment stages. A user is allowed to compare tooth positioning of at least two different treatment stages by displaying the at least two different treatment stages on a screen. The user is then allowed to select an end stage based on comparison of tooth positioning of at least two different stages.

In accordance with another embodiment, a system is provided for comparative orthodontic treatment planning. The system includes a computer coupled to a server, and the computer comprises a processor and a computer readable medium comprising instructions which, if executed, causes the computer to generate at least one treatment plan for a patient based on an initial tooth data set received by the computer. The plan comprises a plurality of planned successive tooth arrangements for moving teeth along a treatment path from an initial arrangement toward a selected final arrangement. The plan also comprises a series of one or more treatment stages to move teeth along the treatment path. The computer readable medium comprising instructions which, if executed, also causes the computer to display tooth arrangements for each of the one or more treatment stages, to allow a user to compare tooth arrangements for at least two different treatment stages, and to allow a user to select a treatment plan after comparing tooth arrangements.

In accordance with yet another embodiment, a method is provided for orthodontic treatment planning using an orthodontic treatment planning system comprising a computer and a comparative treatment planning tool. At the computer, an initial tooth data set comprising an initial tooth arrangement is received. The comparative treatment planning tool and the initial tooth data set are used to generate a plurality of different treatment plans to move teeth from the initial arrangement toward a target arrangement. Each of the treatment plans comprises a plurality of treatment stages. A user is allowed to select a desired treatment plan based on tooth positioning of target arrangements of at least two different treatment plans by simultaneously displaying on a screen the target arrangements of each of at least two different treatment plans.

BRIEF DESCRIPTION OF THE DRAWINGS

The invention, together with further objects and advantages thereof, may best be understood by reference to the following description taken in conjunction with the accompanying drawings in which:

FIG. 6 is a screenshot of a comparative treatment planning tool illustrating a graphical representation of a treatment stage in a treatment plan in accordance with yet another embodiment.

DETAILED DESCRIPTION OF THE PREFERRED EMBODIMENTS

Figure 1:
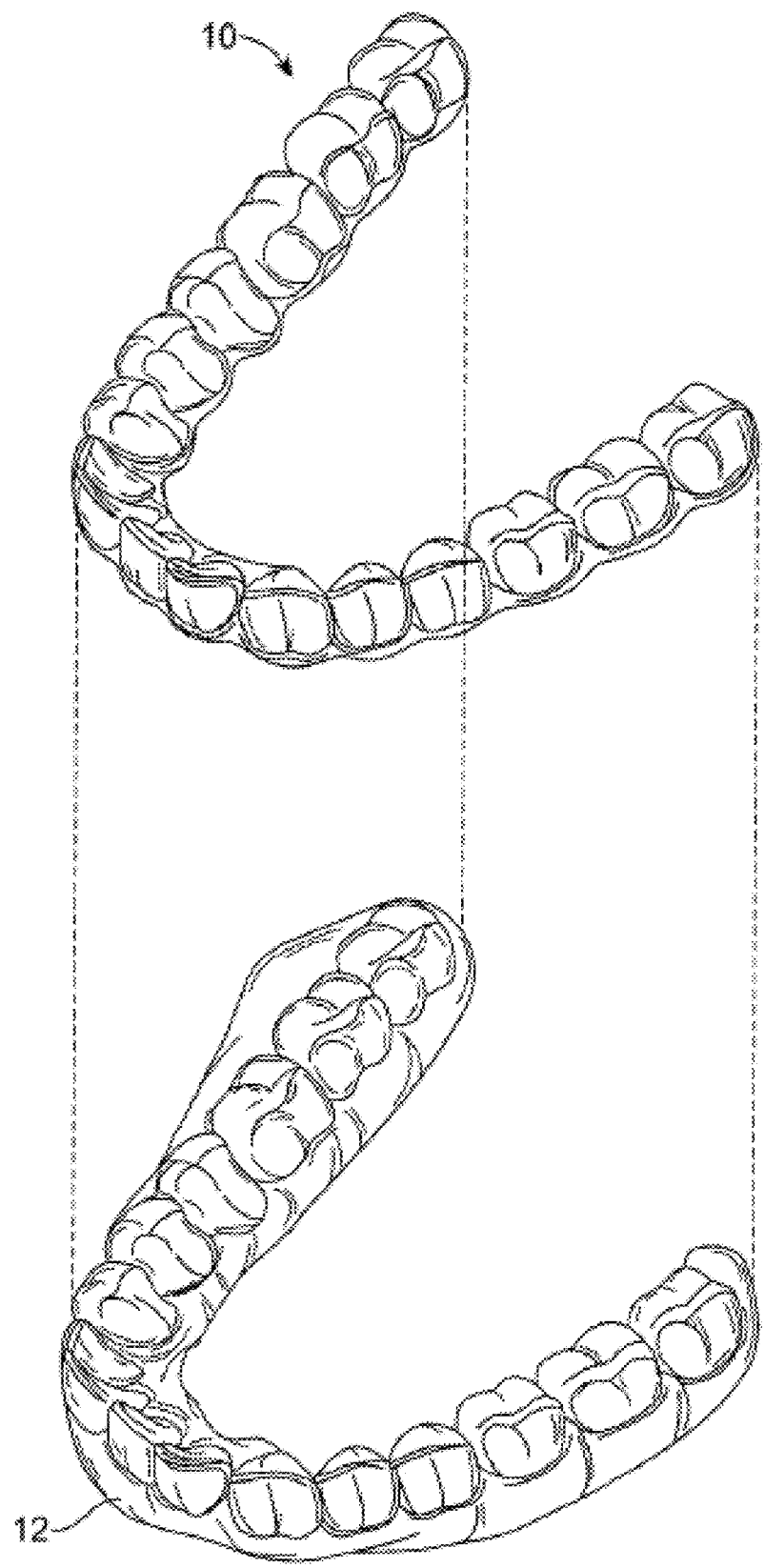
FIG. 1 is a perspective view of a dental appliance in accordance with an embodiment.

The present invention provides improved systems and methods of managing delivery of an orthodontic treatment plan that can be customized for the individual patient being treated. The systems and methods of the present invention include generating one or more treatment plans for a patient and providing additional options for customizing the treatment plans. A comparative orthodontic treatment planning tool provides dentists and orthodontists with the ability to collaborate with patients and fabricators to make informed decisions in orthodontic treatment planning Comparative treatment planning tools described herein provide patients with more opportunity for customization and budget planning, and collaborative decision making with the orthodontist. Orthodontist can also use the comparative treatment planning tools to work with specialists, such as oral surgeons, prosthodontists, and restorative specialists, and generalists can use the comparative treatment planning tools to work with orthodontists and other specialists.

In various embodiments, a comparative treatment planning tool that is used with a computing system can be used in orthodontic treatment planning and the design of dental appliances thereof. Such a computing system may include one or more computing devices having, for example, a processor and memory. The memory can include various types of information including data (e.g., dentition measurement, uploaded scanned tooth data, and/or digital model data) and/or executable instructions to perform the methods discussed herein. Various embodiments can include one or more input and/or output interfaces. Such interfaces can be used, for instance, to connect the computing device with one or more input or output devices. For example, a system may include connectivity to a scanning device, a camera dock, a keyboard, and/or other peripherals.

Some embodiments can include a network interface. Such an interface can allow, for example, for processing on another networked computing device. Such devices can be used to obtain information about the patient or executable instructions for use with various embodiments provided herein, in some instances.

The comparative treatment planning tools described herein provide doctors, patients, and manufacturers with more information as well as additional options in treatment planning, product selection and the ordering process. The comparative treatment planning tools also serve to inform and educate patients with multiple different treatment options (and their respective pricing) along with visual tools that can show predicted teeth arrangements at different stages for different options. The treatment plan can be customized to the individual patient and typically account for patient-specific factors, such as the positioning of the patient's teeth, desired movements, treatment goals and timing, pricing, complexity of treatment, and other clinical considerations.

In addition, the comparative treatment planning tools described herein can improve shipping to doctor, reduction in number of aligners, progress tracking to ensure better treatment outcomes, or material selection for better outcomes. For example, if an orthodontist or dentist decides on partial treatment planning in steps or decides to use different materials or additional or different features for a particular stage, then aligners can be batch shipped for a particular stage of the treatment plan. Thus, the comparative treatment planning tools described herein provide additional flexibility to treatment planners in that treatment planning can be done all at once from beginning to end or treatment planning can be done in particular stages. Even if treatment planning is done in stages, the comparative treatment planning tool still provides an overview of the treatment plan from beginning to end.

FIG. 1 shows an aligner or adjustment appliance 10, which is worn by the patient in order to achieve an incremental repositioning of individual teeth in the jaw 12 as described generally above. The appliance can include a shell (e.g., polymeric shell) having teeth-receiving cavities that receive and resiliently reposition the teeth. Such appliances, including those utilized in the Invisalign® System, are described in numerous patents and patent applications assigned to Align Technology, Inc. including, for example in U.S. Pat. Nos. 6,450,807, and 5,975,893, as well as on the company's website, which is accessible on the World Wide Web (see, e.g., www.align.com). As shown in FIG. 1, the appliance or aligner 10 has a geometry for receiving teeth.

As noted above, aligners have been developed as a more aesthetically pleasing as well as more convenient appliance for straightening teeth. An aligner is a relatively, and typically transparent, thin shell of material that generally conforms to a patient's teeth but is slightly out of alignment with the current (i.e., initial) tooth configuration. The material of the aligner is typically a polymeric material that has resilient properties. Dental treatments using aligners typically involve repositioning misaligned teeth and changing bite configurations for improved cosmetic appearance and dental function. Such repositioning with aligners can be accomplished by applying controlled forces to one or more teeth over a period of time.

As shown in FIG. 1, the appliance 10 can be configured to fit over an entire dental arch 12. In other embodiments, the appliance may be designed to fit over some or all of the teeth in the upper or lower jaw. In some embodiments, the appliance is a removable orthodontic tooth positioning appliance having teeth receiving cavities shaped to directly receive at least some of the patient's teeth and apply a resilient positioning force to the patient's teeth. In some cases, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth that are moved can also serve as a base or anchor for holding the appliance as it is worn by the patient.

Typically, no wires or other means will be provided for holding an appliance in place over the teeth. In some cases, however, it may be desirable or necessary to provide individual anchors on teeth with corresponding receptacles or apertures in the appliance so that the appliance can apply a selected force on the tooth. Exemplary appliances are described in numerous patents and patent applications assigned to Align Technology, Inc. including, for example, in U.S. Pat. Nos. 6,450,807, and 5,975,893, as well as on the company's website, which is accessible on the World Wide Web (see, e.g., www.invisalign.com). The aforementioned patents are hereby incorporated herein for all purposes.

An appliance can be designed and/or provided as part of a set of a plurality of appliances. In such an embodiment, each appliance may be configured such that a tooth-receiving cavity has a geometry corresponding to an intended intermediate or final tooth arrangement. The patient's teeth can be progressively repositioned from an initial tooth arrangement to a target tooth arrangement by placing a series of incremental position adjustment appliances over the patient's teeth. A target tooth arrangement is a planned tooth arrangement (e.g., a planned temporary or final arrangement) selected for the patient's teeth at a specific stage of the planned orthodontic treatment. A target arrangement can be one of many intermediate arrangements for the patient's teeth during the course of orthodontic treatment, which may include where surgery is recommended, where inter-proximal reduction (IPR) is appropriate, where extraction is appropriate, where a progress check is scheduled, where anchor placement is best, where palatal expansion is desirable, etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Each appliance may be configured so that its tooth-receiving cavity has a geometry corresponding to an intermediate or final tooth arrangement intended for the appliance. The patient's teeth are progressively repositioned from their initial tooth arrangement to a final tooth arrangement by placing a series of incremental position adjustment appliances over the patient's teeth. The adjustment appliances can be generated all at the same stage or in sets or batches, e.g., at the beginning of a stage of the treatment. A set of different appliances can be designed and fabricated prior to the patient wearing any appliance in the set. The patient wears each appliance for a set period of time or until the pressure of each appliance on the teeth is minimal or can no longer be felt. At that point, the patient replaces the current adjustment appliance with the next adjustment appliance in the series until no more appliances remain. The appliances are generally not affixed to the teeth so as to require removal by a practitioner (e.g., patient removable) and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to increase the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

Individual aspects of a treatment planning process are discussed in further detail below. The process includes generating a treatment plan for repositioning a patient's teeth. Briefly, a treatment plan will include obtaining data comprising an initial arrangement of the patient's teeth, which typically includes obtaining an impression or scan of the patient's teeth prior to the onset or start of treatment. The treatment plan will also include identifying a desired final arrangement of the patient's teeth, as well as a plurality of planned successive or intermediary tooth arrangements for moving the teeth along a treatment path from the initial arrangement toward the selected final arrangement. As noted, treatment can be pre-planned for administration to a patient in a series of one or more treatment phases, with a phase including a set of appliances that are worn successively by the patient to reposition the teeth through planned arrangements and eventually toward a selected final arrangement.

The adjustment appliances can be generated all at the same stage or in sets or batches, e.g., at the beginning of a stage of the treatment, and the patient wears each appliance until the pressure of each appliance on the teeth can no longer be felt or has resulted in the maximum amount of expressed tooth movement for that given stage. A plurality of different appliances (e.g., set) can be designed and even fabricated prior to the patient wearing any appliance of the appliances. After wearing an appliance for an appropriate period of time, the patient replaces the current appliance with the next appliance in the series until no more appliances remain. The appliances are generally not affixed to the teeth and the patient may place and replace the appliances at any time during the procedure (e.g., patient-removable appliances).

The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

The appliance 10 can be fabricated using a variety of different suitable methods, including thermoforming, casting, 3D printing, stereolithography, milling, direct fabrication etc. For example, methods for making the appliances can include thermoforming a polymer sheet into an aligner by heating the sheet and then molding the sheet to a particular configuration. Exemplary methods for fabricating the appliances are described in numerous patents and patent applications assigned to Align Technology, Inc. including, for example, in U.S. application Ser. No. 13/186,374 as well as on the company's website, which is accessible on the World Wide Web (see, e.g., www.invisalign.com). The aforementioned patent application is hereby incorporated herein for all purposes.

As noted above, placement of an appliance over the teeth provides controlled forces in specific locations to gradually move the teeth into a new configuration and repetition of this process with successive appliances that provide progressive configurations eventually move the teeth through a series of intermediate arrangements to a target, prescribed, or desired arrangement. An example of such a system is described in U.S. Pat. No. 5,975,893, which is hereby incorporated herein by reference. Appliances can be generated based on the planned arrangements and will be provided to the practitioner and ultimately administered to the patient. The appliances are typically provided and/or administered in sets or batches of appliances, such as 2, 3, 4, 5, 6, 7, 8, 9, or more appliances, but are not limited to any particular administrative scheme.

Figure 2:
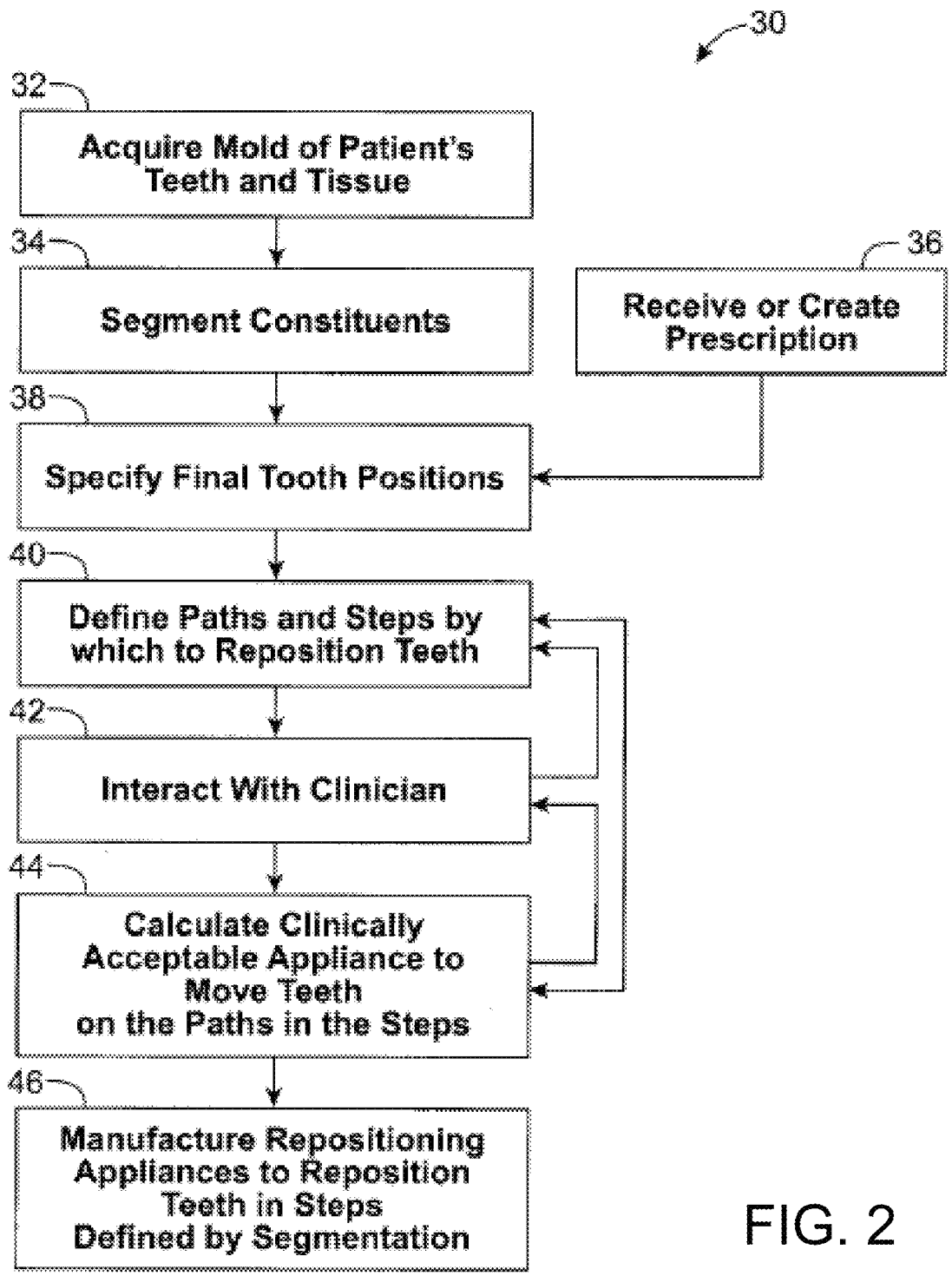
FIG. 2 is a flow chart of a process for treatment planning and fabrication of orthodontic appliances in accordance with an embodiment.

FIG. 2 illustrates the general flow of an exemplary process 30 for defining and generating a treatment plan, including repositioning appliances for orthodontic treatment of a patient. The steps of the process can be implemented as computer program modules for execution on one or more computer systems. As an initial step, an initial digital data set of the patient's teeth is created. To create the initial digital data set, a mold or a scan of a patient's teeth or mouth tissue is acquired (Step 32). Creating the initial digital data set generally involves taking casts of the patient's teeth and gums, and may in addition or alternately involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents an initial (e.g., pretreatment) arrangement of the patient's teeth and other tissues.

The initial digital data set, which may include both raw data from scanning operations and data representing surface models derived from the raw data, is processed to segment the tissue constituents from each other (Step 34), including defining discrete dental objects. For example, data structures that digitally represent individual tooth crowns can be produced. In some embodiments, digital models of entire teeth are produced, including measured or extrapolated hidden surfaces and root structures.

The desired final position of the teeth that is, the desired and intended end result of orthodontic treatment, can be calculated from basic orthodontic principles, or can be extrapolated computationally from a clinical prescription (Step 36). With a specification of the desired final positions of the teeth and a digital representation of the teeth themselves, the final position and surface geometry of each tooth can be specified (Step 38) to form a complete model of the teeth at the desired end of treatment. Generally, in this step, the position of every tooth is specified. The result of this step is a set of digital data structures that represents a desired and/or orthodontically correct repositioning of the modeled teeth relative to presumed-stable tissue. The teeth and tissue are both represented as digital data.

Having both a beginning position and a final position for each tooth, the process next defines a treatment path or tooth path for the motion of each tooth (Step 40). This includes defining a plurality of planned successive tooth arrangements for moving teeth along a treatment path from an initial arrangement to a selected final arrangement. In one embodiment, the tooth paths are optimized in the aggregate so that the teeth are moved in the most efficient and clinically acceptable fashion with the least amount of round-tripping to bring the teeth from their initial positions to their desired final positions. Round-tripping is any motion of a tooth in any direction other than directly toward the desired final position. Round-tripping is sometimes necessary to allow teeth to move past each other. The tooth paths are segmented. The segments are calculated so that each tooth's motion within a segment stays within threshold limits of linear and rotational translation. In this way, the end points of each path segment can constitute a clinically viable repositioning, and the aggregate of segment end points constitute a clinically viable sequence of tooth positions, so that moving from one point to the next in the sequence does not result in a collision of teeth. [In one embodiment, the comparative treatment planning tool allows the user to choose whether the tooth paths include round-tripping, and if so, how much round-tripping. It may be possible to stop treatment before any (significant) round tripping is necessary. In some cases, the orthodontist or dentist can provide for IPR or extraction in the treatment plan instead. In this example, the comparative treatment planning tool can also allow the orthodontist or dentist to see a comparison of round-tripping versus IPR or extraction, and then select the better option after seeing the comparison. Thus, it will be understood that there may be different treatment paths for the same initial and final position of a tooth.

The threshold limits of linear and rotational translation are initialized, in one implementation, with default values based on the nature of the appliance to be used. More individually tailored limit values can be calculated using patient-specific data. The limit values can also be updated based on the result of an appliance-calculation, which may determine that at one or more points along one or more tooth paths, the forces that can be generated by the appliance on the then-existing configuration of teeth and tissue is incapable of affecting the repositioning that is represented by one or more tooth path segments. With this information, paths or the affected sub-paths can be recalculated.

At various stages of the process, the process can include interaction with a clinician responsible for the treatment and/or the patient (Step 42). The interaction can be implemented using a comparative treatment planning tool, as described herein, programmed to receive tooth positions and models, as well as path information. The comparative treatment planning tool is advantageously programmed to allow the clinician to display multiple different animations of the positions and paths and to allow the clinician to reset the final positions of one or more of the teeth and to specify constraints to be applied to the segmented paths. If the clinician makes any changes, certain steps of the process are performed again to recalculate paths.

The tooth paths and associated tooth position data are used to calculate clinically acceptable appliance configurations (or successive changes in appliance configurations) that will move the teeth on the defined treatment path in the steps specified (Step 44). Each appliance configuration corresponds to a planned successive arrangement of the teeth, and represents a step along the treatment path for the patient. The steps are defined and calculated so that each discrete position can follow by straight-line tooth movement or simple rotation from the tooth positions achieved by the preceding discrete step and so that the amount of repositioning required at each step involves an orthodontically optimal amount of force on the patient's dentition. As with other steps, this calculation step can include interactions with the clinician and/or patient (Step 42).

Having calculated appliance definitions, the process 30 can proceed to the manufacturing step (Step 46) in which appliances defined by the process are manufactured, or electronic or printed information is produced that can be used by a manual or automated process to define appliance configurations or changes to appliance configurations. Appliances according to the treatment plan can be produced in entirety, such that each of the appliances is manufactured (e.g., prior to treatment), or can be manufactured in sets or batches. For example, in some cases it might be appropriate to manufacture an initial set of appliances at the outset of treatment with the intention of manufacturing additional sets of appliances (e.g., second, third, fourth, etc.) after treatment has begun (e.g., as discussed further herein). For example, a first set of appliances can be manufactured and administered to a patient. Following administration, it may be desirable to inspect the progression of the patient's teeth along the treatment path before manufacturing and/or administering subsequent set(s) of appliances. In some cases, it may be desirable to modify the treatment plan before manufacturing subsequent set(s) of appliances.

Generating and/or analyzing digital treatment plans, as discussed herein, can include, for example, use of three-dimensional orthodontic treatment planning tools, such as ClinCheck® from Align Technology, Inc. Such treatment planning tools allow the clinician to use the actual patient's dentition as a starting point for customizing a treatment plan. The ClinCheck® technology uses a patient-specific digital model to plot a treatment plan, and then uses a processed (e.g., segmented) scan of the achieved treatment outcome, as discussed in U.S. Pat. Nos. 7,156,661 and 7,077,647, which are hereby incorporated herein for all purposes.

The design of the aligners can rely on computer modeling of a series of planned successive tooth arrangements, and the individual aligners are designed to be worn over the teeth and elastically reposition the teeth to each of the planned tooth arrangements.

The theory of orthodontic treatment is not universally agreed upon, and actual treatment and outcomes are subject to additional uncertainties of measurement of patient variables, of relationships to unmeasured patient variables, as well as of varying patient compliance and different patient goals. As a result, different clinicians might prefer different treatment plans for a single patient. Thus, a single treatment plan may not be accepted by every clinician since there is no universally accepted "correct" treatment plan. Additionally, some patients may prefer a less complex treatment plan, less expensive option, or one with a shorter treatment duration. For example, a treatment plan may require surgery in addition to the use of a set of aligners and an alternative treatment plan might involve only treatment with aligners. Some patients may opt not to have surgery and use only aligners to achieve a goal that is close enough to the ideal treatment outcome. In another example, a patient might have a date (e.g., a wedding or graduation) by which the patient would like to have his or her teeth straightened. In such a case, the patient might choose a treatment plan that has a shorter duration but still an acceptable result.

Embodiments of the treatment planning tool described herein allow the clinician to obtain a single initial data set of the patient's initial tooth arrangement and provide the clinician with different options for treatment planning to give both the clinician and patient more flexibility and treatment options. The treatment planning tool also serves to educate the patient with a visual tool to view different treatment options, based on factors, such as the complexity of treatment, pricing of the treatment, duration of the treatment, material selection, attachment selection, etc.

Referring to FIGS. 3-6, embodiments of a comparative orthodontic treatment planning tool for designing a series of polymeric shell appliances will be described. FIG. 3A shows a screen shot 50 of a comparative treatment planning tool illustrating a graphical representation of a treatment stage in a treatment plan according to an embodiment. In the example shown in FIG. 3A, the comparative treatment planning tool shows the predicted tooth positioning of the treatment plan at "Stage 12." The treatment planning tool allows the user (i.e., clinician and/or patient) to see the predicted tooth positioning for a particular stage of the treatment based on the initial data set obtained. For example, the screenshot shown in FIG. 3A shows the predicted tooth positioning at "Stage 12" of a 24 stage treatment plan. In the illustrated example, the treatment planning tool allows the user to use the scroll bar at the bottom of the screen to toggle between stages to view the predicted tooth positioning at each stage. In this example, the user can then select between a 12 stage treatment plan and a 24 stage treatment plan. The 12 stage treatment plan typically costs less for the patient than the 24 stage treatment plan, and also likely has a shorter treatment length. The cost and time savings for the doctor, lab fee, and even the patient could be significant as compared to the 24 stage treatment plan. However, the tooth positioning achieved in the 12 stage treatment plan may not be as ideal as the positioning that can be achieved by the 24 stage treatment plan. According to an embodiment, the comparative treatment planning tool allows the user to toggle between the initial stage (Stage 0) and Stage 12, between the initial stage and the final stage (Stage 24), and between Stage 12 and the final stage.

Figure 3A:
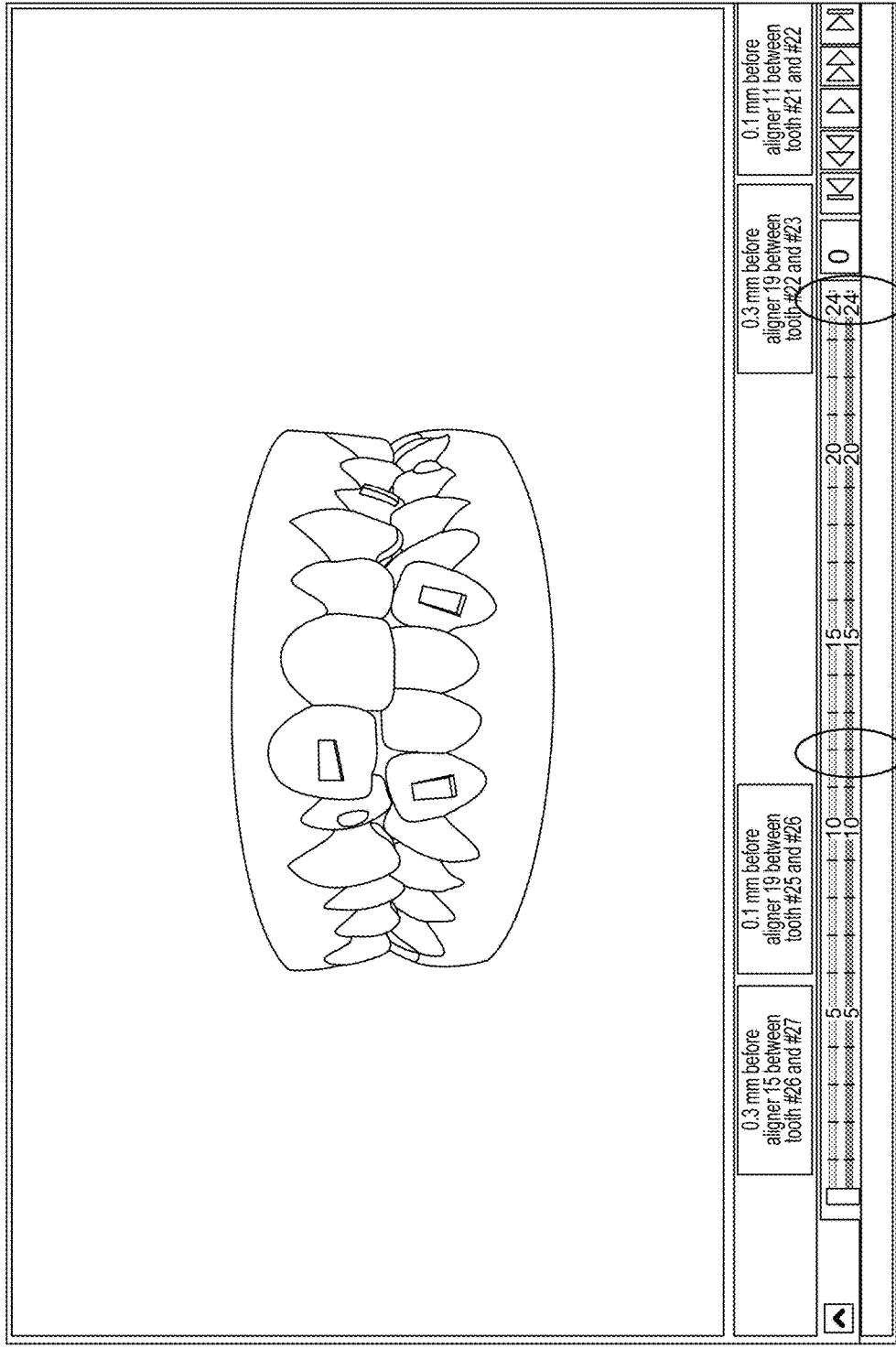
FIG. 3A is a screenshot of a comparative treatment planning tool illustrating a graphical representation of a treatment stage in a treatment plan in accordance with an embodiment.
Figure 3B:
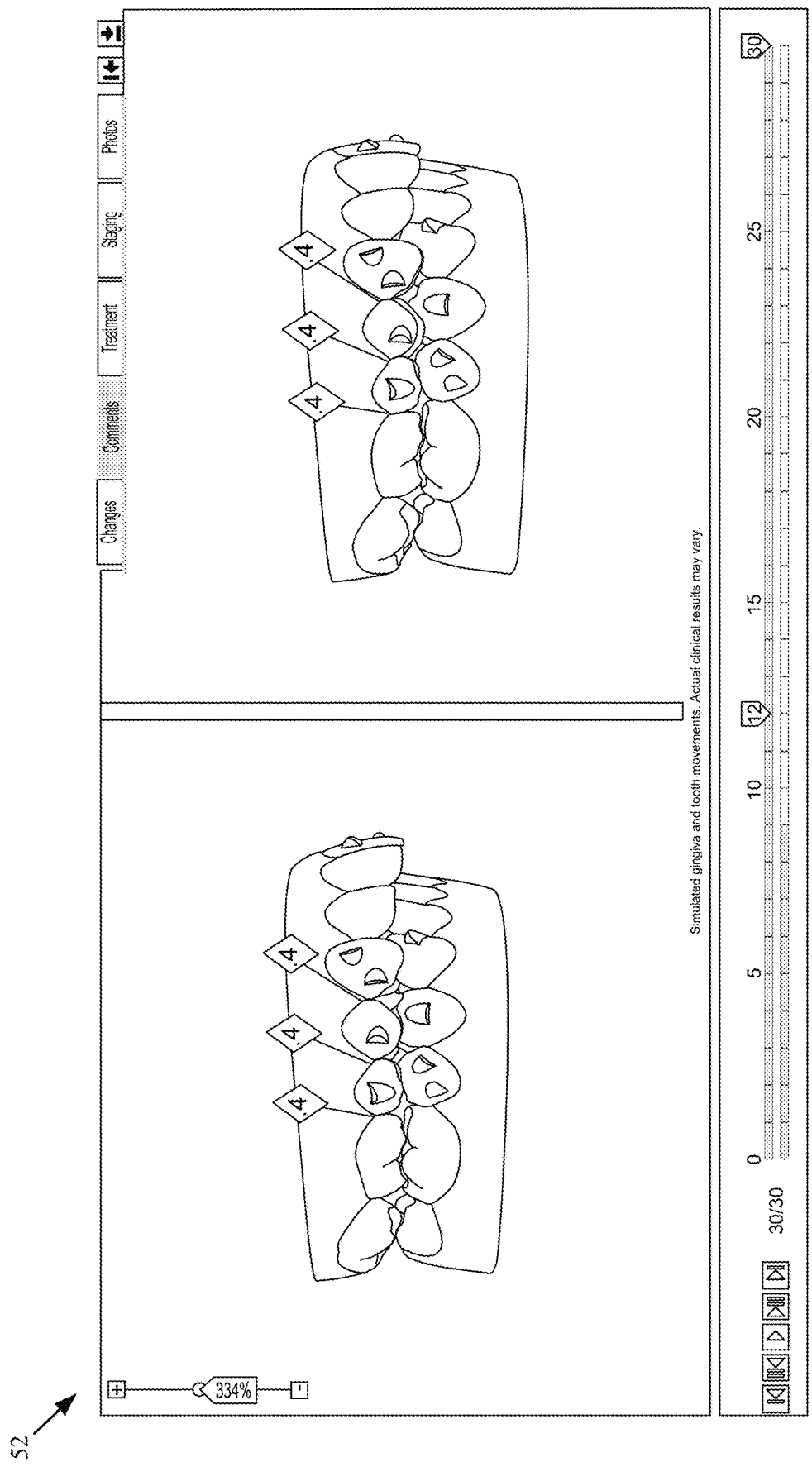
FIG. 3B is a screenshot of a comparative treatment planning tool illustrating a graphical representation of a split screen screenshot comparing different treatment stages in accordance with an embodiment
Figure 3C:
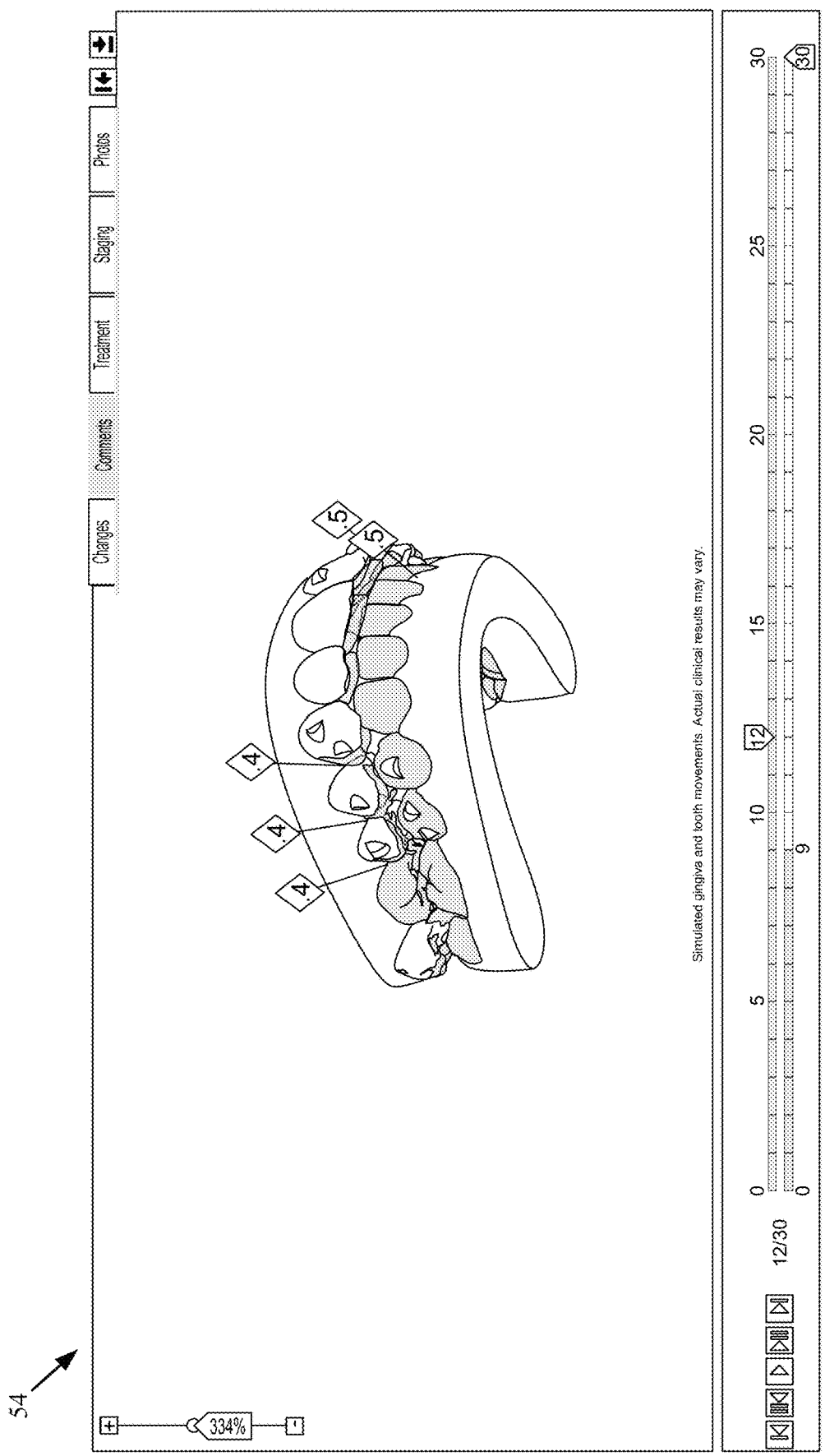
FIG. 3C is a screenshot of a comparative treatment planning tool illustrating a graphical representation of a treatment stage superimposed over another treatment stage in accordance with an embodiment.

In another embodiment, as shown in FIG. 3B, the comparative treatment planning tool can also provide a split screen to allow a dentist or orthodontist to compare different stages from the same treatment plan or from different treatment plans. In the exemplary screenshot 52 shown in FIG. 3B, a split screen shows the predicted positions of the teeth at Stage 12 on the left side and the predicted positions of the teeth at the final stage (Stage 30) on the right side. In the illustrated embodiment, the two stages shown in the split screen are from the same treatment plan. However, it will be understood that the comparative treatment planning tool can provide a split screen to compare different stages from different treatment plans. The split screen allows a side-by-side comparison of different stages (either from the same treatment plan or from different treatment plans).

In another embodiment, the comparative treatment planning tool can superimpose the predicted tooth positioning of one stage over the predicted tooth positioning of another stage to allow the user to see the difference between the stages (either from the same treatment plan or from different treatment plans). As shown in the screenshot 54 of FIG. 3C, the teeth can be shaded or colored differently for each stage and the different stages can be superimposed over one another so that the patient and/or clinician can see the difference of the tooth positioning between the stages.

As noted above, toggling, superimposing, and split screens can also provide comparisons of stages from different treatment plans. For example, one treatment plan may include IPR or extraction and another treatment plan does not have IPR or extraction, and the comparative treatment planning tool can be used to compare the final (or an intermediate stage) stages of the two treatment plans. In some cases, the difference between Stage 24 may not be significant enough for a patient and/or clinician to spend the additional time and/or money for the patient's teeth to reach the predicted final stage. If the patient and/or clinician decide the difference is not worth the additional expense and time, then the user can click the "Accept here" button for Stage 12, as shown in FIG. 3A. If, after comparing Stage 12 and Stage 24, the patient and/or clinician decide that it is worth the additional expense and time for the patient's teeth to reach the predicted final stage, the user can click the "Accept here" button for Stage 24, as shown in FIG. 3A. It will be understood that, in this embodiment, the tooth movement routes are the same, whether the user chooses to stop at Stage 12 or Stage 24.

According to an embodiment, the comparative treatment planning tool also allows the clinician to view multiple comparative treatment plans with restorative treatment in addition to orthodontic treatment. For example, clinician may be able to see that, at Stage 12, the teeth are not in the ideal positions with only orthodontic treatment. The comparative treatment planning tool also allows the clinician to add restorative treatment to the plan and the treatment planning tool can provide a comparison at a stage (e.g., Stage 12) of the teeth with and without the restorative treatment. Thus, if the clinician and/or patient can decide whether the restorative treatment is worth it. The comparative treatment planning tool helps clinicians and patients make better choices by providing different options and allowing comparison of the different options.

Figure 4:
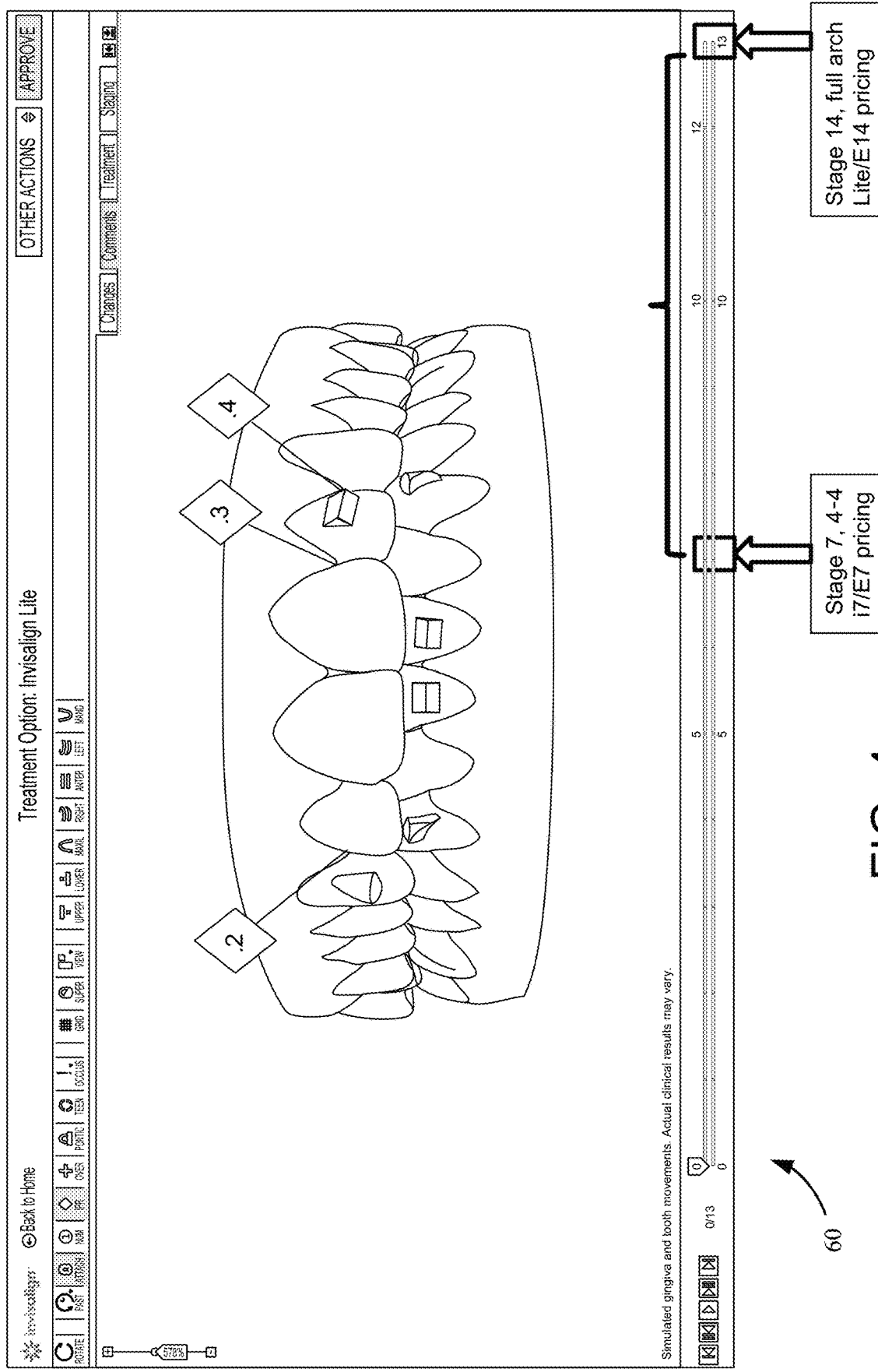
FIG. 4 is a screenshot of a comparative treatment planning tool illustrating a graphical representation of a treatment stage in a treatment plan in accordance with a different embodiment.

In another embodiment, the planning tool allows the user to select a treatment plan based the number of stages in a treatment plan where the tooth movement routes may differ from plan to plan. In this embodiment, the different treatment plans are also generated from a single initial data set. For example, FIG. 4 shows a screen shot 60 of a comparative treatment planning tool illustrating a graphical representation of a treatment stage in a treatment plan according to another embodiment. In this embodiment of the treatment planning tool, different treatment plans having different tooth movement routes or paths are provided and compared so that the treatment provider and/or patient can choose from different treatment plans/approaches based on the individual's needs. In the illustrated example, the scroll bar at the bottom of the screen shot 60 shows two different stages from two different treatment plans that can be compared: "Stage 7, 4-4, i7/E7 pricing" and "Stage 14, full arch, Lite/E14 pricing." For example, in one treatment plan, there can be posterior movement in addition to anterior movement whereas the movement in another treatment plan is limited to only anterior movement. In the screenshot 60 in FIG. 4, Stage 7 and Stage 14 of the same treatment plan can be selected to see the predicted tooth positioning at these stages of the treatment plan. At the same time, the user can also see the respective pricing if these stages are selected to be the final stage of the treatment plan. In this example, the pricing at Stage 14 of the "4-4" treatment plan is more than if the same treatment is stopped at Stage 7. It will be understood that the "4-4" treatment plan is only an example. The treatment plan could be for any subgroup of teeth and any number of stages, and any combination thereof. For example, the treatment plan could be for "3-3" (anterior teeth only) or "5-5" or "7-7." It will also be understood that the pricing terms (i.e., "i7/E7 pricing" and "Lite/E14 pricing") used in the illustrated example of FIG. 4 are also only examples and are provided to illustrate that the comparative treatment planning tool can also provide relative pricing for different stages on the screen.

The screenshot 60 of FIG. 4 also shows Stage 14 of a treatment plan for the full arch (i.e., both anterior and posterior movement) and its pricing. The comparative treatment planning tool provides comparison of the different treatment stages of different treatment plans by allowing toggling between the treatment stages or superimposition of different stages over one another, as noted above. Although only Stage 7 and Stage 14 are shown in the illustrated screenshot 60, it will be understood that the user can select the number of stages for a treatment plan. Alternatively, the user can specify the desired pricing range and the treatment planning tool can provide the treatment plan options in which the number of stages and/or tooth movement routes can be selected for the desired pricing range.

Figure 5:
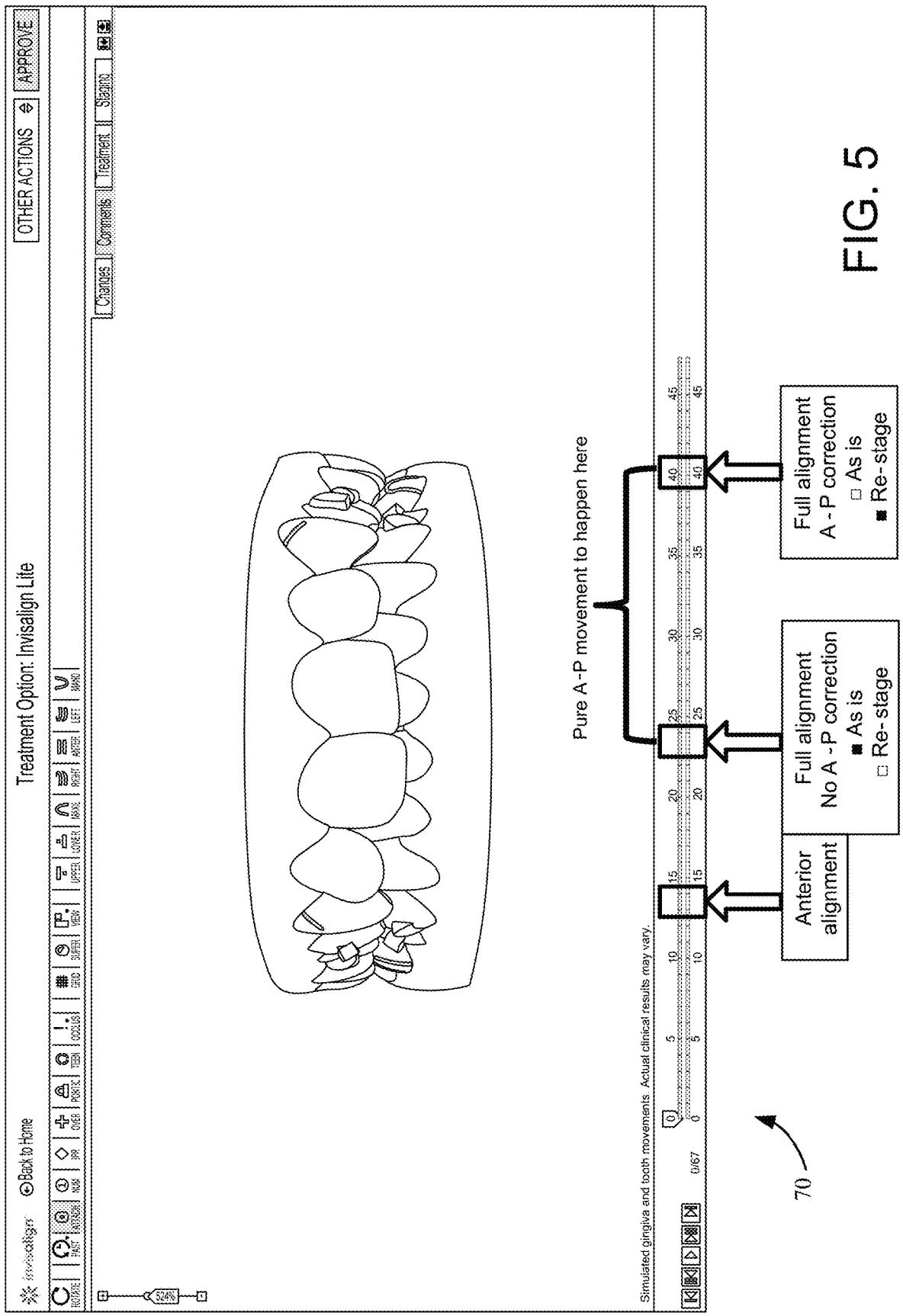
FIG. 5 is a screenshot of a comparative treatment planning tool illustrating a graphical representation of a treatment stage in a treatment plan in accordance with another embodiment.

FIG. 5 shows a screen shot 70 of a comparative treatment planning tool illustrating a graphical representation of a treatment stage in a treatment plan according to yet another embodiment. In this embodiment, the comparative treatment planning tool provides different treatment plans from a single initial data set based on a treatment goal provided by the user. For example, a treatment goal of anterior alignment only can be provided. Alternatively, a treatment goal of full alignment can be provided. In some cases, a patient might choose to align only the teeth in the top arch as opposed to both the top and bottom arches. The user can use the treatment planning tool to compare the tooth positioning at various stages. Once the treatment provider determines which accept point to select, based on the complexity of treatment goal the patient wants to achieve, there would be different options, as described below.

One option is to manufacture aligners as is, with consecutive treatment goals being achieved (e.g., treatment would first achieve anterior alignment, then full alignment, then bite relationship correction, not having simultaneous movements, i.e. correcting anterior alignment while correcting class II). Another option is to re-stage the treatment with the final accept point as the sole treatment goal, thereby potentially skipping and/or consolidating previous accept point and therefore shortening treatment time. In the example provided, a re-staged treatment plan might achieve anterior and posterior alignment at the same time instead of consecutively. Or, a re-staged plan might begin with anterior alignment, then posterior alignment, and finish with more anterior alignment. The re-staging can be done to most efficiently move the teeth to reach the end goal. Different re-staged treatment plans (having different routes and/or alignment options) could be provided, depending on the patient's goals. If the patient has a date by which he or she would like anterior alignment (e.g., for a wedding), then, in the provided example, the treatment may not need to be re-staged and the anterior alignment would take place first. Yet another option is to provide restorative treatment at certain stages in addition to orthodontic treatment versus orthodontic treatment only throughout the treatment plan. It will be understood that the comparative treatment planning tool can be used to provide other treatment plans to allow a clinician to compare the different treatment plans and select one based on treatment duration, complexity, pricing, etc.

Figure 6:
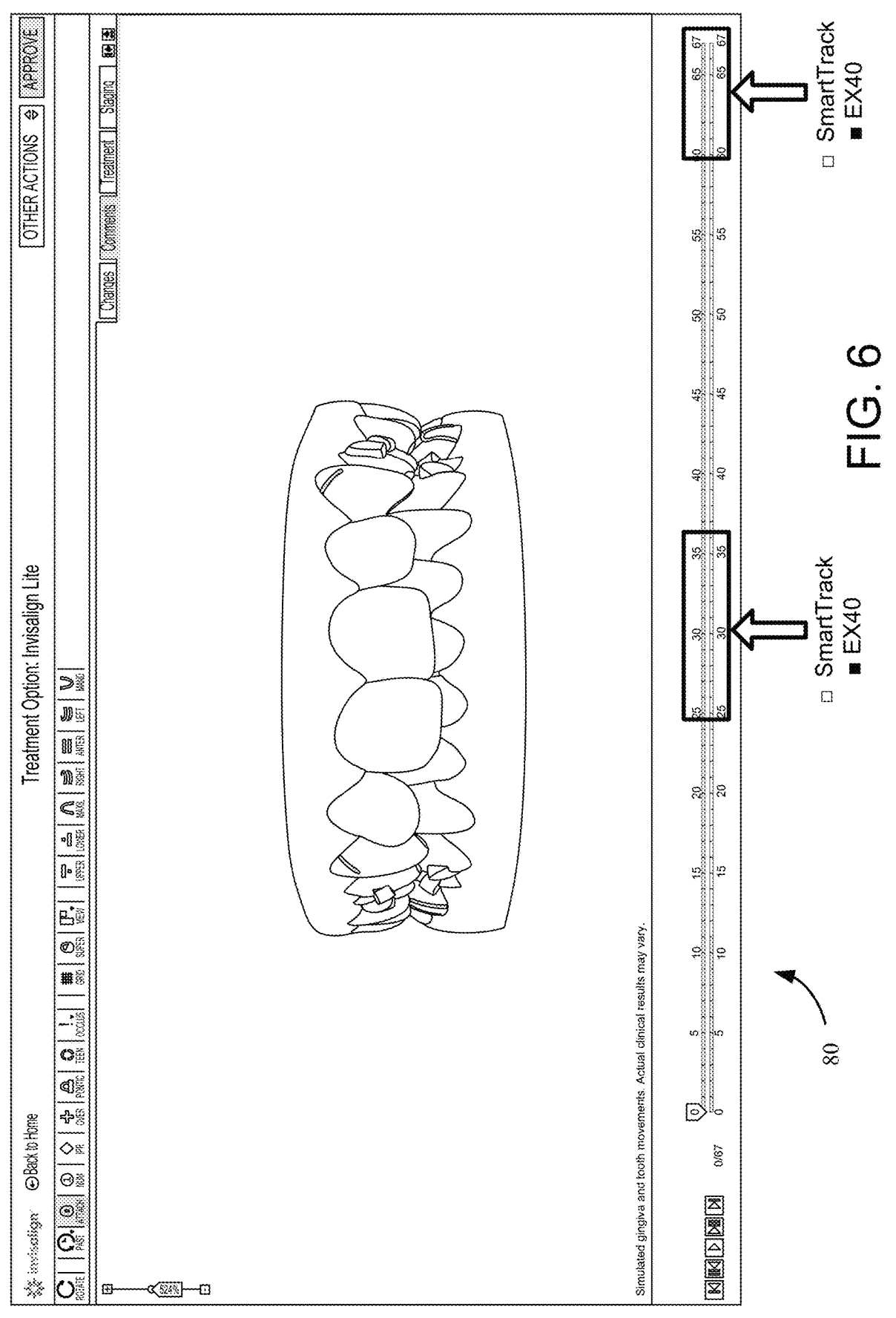

FIG. 6 shows a screen shot 80 of a comparative treatment planning tool illustrating a graphical representation of a treatment stage in a treatment plan according to another embodiment. According to the example shown in FIG. 6, the user can select different materials for aligners to achieve different types as well as different rates of movements. The treatment planning tool can provide the user with multiple accept points for batch shipping based on the material selected. For example, the aligners can be formed of a first material in Stages 1-14, a different material for Stages 15-20, and yet another material for Stages 21-24. In another example, the user can also select different features and attachments. Features and/or attachments can be used to change the shape of an aligner to achieve different types and/or rates of tooth movements. Attachments can include different geometric shapes, such as ovoid, tear-drop, ramp, hexagonal, and/or rectangular, and other shapes. The attachment elements can, for example, provide friction between the aligner and the teeth to increase retention of the aligner. That is, the attachment elements can create greater retention of the aligner on the teeth in a particular direction.

Figure 7:
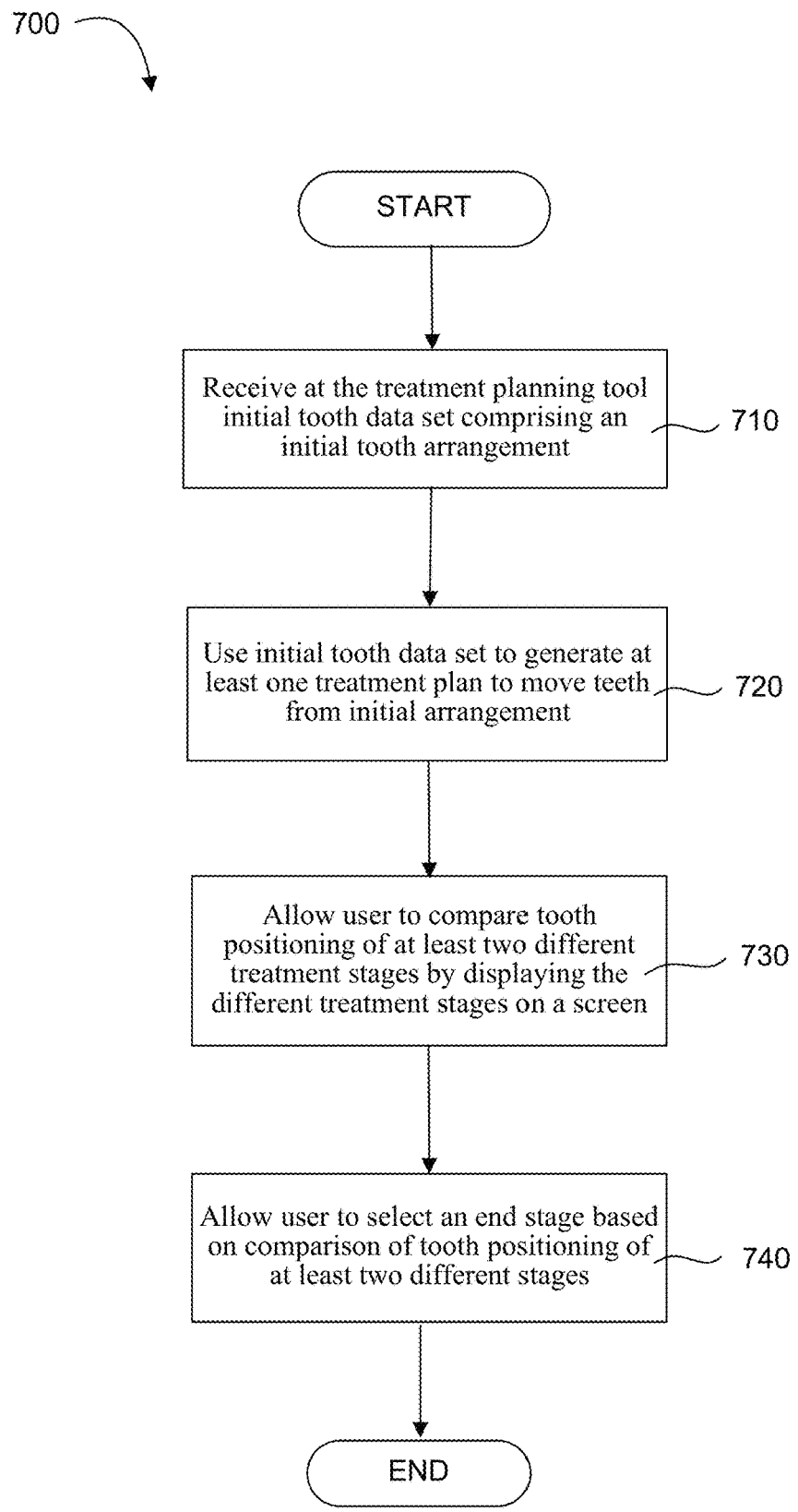
FIG. 7 is a flow chart illustrating a method of orthodontic treatment planning with a comparative orthodontic treatment planning tool in accordance with an embodiment.

A method 700 of orthodontic treatment planning with a comparative orthodontic treatment planning tool will be described with reference to FIG. 7 and steps 710-740. In step 710, an initial tooth data set comprising an initial tooth arrangement is received at the treatment planning tool. In step 720, the initial tooth data set is used to generate at least one treatment plan to move teeth from the initial arrangement. Each treatment plan includes a plurality of treatment stages. A user is then allowed to compare the tooth positioning of at least two different treatment stages by displaying the at least two different treatment stages on a screen in step 730. The different treatment stages can be displayed either simultaneously (e.g., split screen display or superimposition of the different stages) or consecutively (e.g., toggling between displays of the different stages). In step 740, the user is allowed to select an end stage based on a comparison of tooth positioning of at least two different stages.

Figure 8:
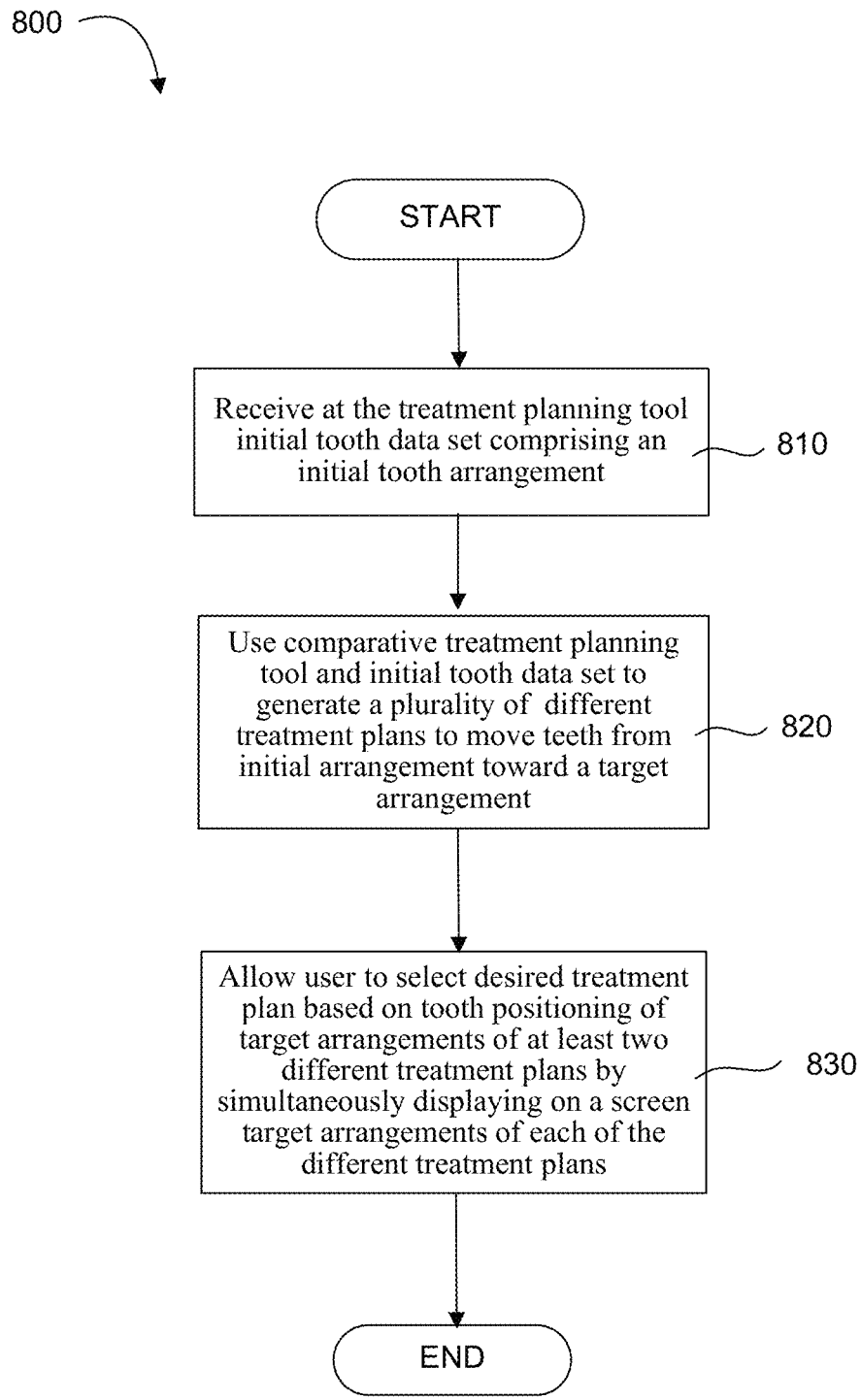
FIG. 8 is a flow chart illustrating a method of orthodontic treatment planning using an orthodontic treatment planning system comprising a computer and a comparative treatment planning tool in accordance with an embodiment.

A method 800 of orthodontic treatment planning using an orthodontic treatment planning system comprising a computer and a comparative treatment planning tool will be described with reference to FIG. 8 and steps 810-830. In step 810, an initial tooth data set comprising an initial tooth arrangement is received at the computer. In step 820, the comparative treatment planning tool and the initial tooth data set are used to generate a plurality of different treatment plans to move teeth from the initial arrangement toward a target arrangement. Each of the treatment plans includes a plurality of treatment stages. In step 830, a user is allowed to select a desired treatment plan based on tooth positioning of target arrangements of at least two different treatment plans by simultaneously displaying on a screen the target arrangements of each of at least two different treatment plans.

The embodiments of the comparative treatment planning tool described herein allow patients and/or orthodontists to compare different treatment plans to determine the best treatment plan for the patient, based on different factors, such as time, cost, complexity, materials, etc. According to some embodiments, the treatment planner, such as a dentist or an orthodontist, receives a single input or set up for a particular patient. The set up includes the tooth data of the initial arrangement of the patient's teeth. Based on this single set up, the treatment planner and/or the patient can see and compare and then choose from different treatment options. The decision making can be based on one or more of the factors described herein.

In some embodiments, the treatment provider and/or patient can choose from different treatment plans based on the number of aligners desired. For example, if a patient desires a relatively short treatment duration, the treatment provider may choose a treatment plan that has relatively few aligners but provides significant tooth alignment (e.g., anterior alignment) to still achieve a noticeable and acceptable result. The incremental improvement of the appearance of the teeth that can be achieved with additional treatment stages (and aligners) may not be worth the added time (and expense) for some patients. Some patients, on the other hand, may want to take the time (and spend the money) to achieve the best outcome possible. The treatment provider and/or patient can also choose from different materials for aligners as well as different features, attachments, and shapes for the aligners. In some cases, the patient may want a treatment plan having a short duration to improve the appearance of his or her teeth for an event (e.g., wedding) and then continue treatment later.

Although only a few embodiments of the invention have been described in detail, it should be appreciated that the invention may be implemented in many other forms without departing from the spirit or scope of the invention. In view of all of the foregoing, it should be apparent that the present embodiments are illustrative and not restrictive and the invention is not limited to the details given herein, but may be modified within the scope and equivalents of the appended claims.

What is claimed is:

1. A method of orthodontic treatment planning with a comparative orthodontic treatment planning tool comprising a processor and memory, the method comprising:

receiving, at the treatment planning tool, an initial tooth data set comprising an initial tooth arrangement;

generating, by the treatment planning tool a plurality of treatment plans to move teeth from the initial tooth arrangement based on the initial tooth data set, wherein:

each of the plurality of treatment plans comprises a plurality of orthodontic appliance treatment stages including an initial orthodontic appliance treatment stage, a final orthodontic appliance treatment stage, and a plurality of intermediate orthodontic appliance treatment stages, and is generated prior to displaying any of the plurality of intermediate orthodontic appliance treatment stages of the plurality of treatment plans to a dental practitioner, a first treatment plan of the plurality of treatment plans includes a first number of intermediate orthodontic appliance treatment stages, a second treatment plan of the plurality of treatment plans includes a second number of intermediate orthodontic appliance treatment stages different from the first number of intermediate orthodontic appliance treatment stages, and each of the plurality of intermediate orthodontic appliance treatment stages and each final orthodontic appliance treatment stage corresponds to a different orthodontic appliance;

receiving a user input, wherein the user input specifies at least one constraint for a desired orthodontic treatment plan;

providing at least two different treatment plans of the plurality of treatment plans, wherein both of the at least two different treatment plans meet the at least one constraint specified by the user input;

simultaneously displaying, with the treatment planning tool, three-dimensional models of tooth positioning of at least two different intermediate orthodontic appliance treatment stages from the at least two different treatment plans of the plurality of treatment plans on a screen for comparison by the dental practitioner, the at least two different intermediate orthodontic appliance treatment stages including a first intermediate orthodontic appliance treatment stage from the first treatment plan and a second intermediate orthodontic appliance treatment stage from the second treatment plan;

receiving, at the treatment planning tool, a selection of a final orthodontic appliance treatment stage based on the comparison of tooth positioning of the at least two different intermediate orthodontic appliance treatment stages and after displaying the at least two different intermediate orthodontic appliance treatment stages; and administering, to a patient, one or more of the different orthodontic appliances corresponding to the intermediate orthodontic appliance treatment stages of the treatment plan corresponding to the selected final orthodontic appliance treatment stage.

2. The method of claim 1, further comprising providing relative pricing of the plurality of treatment plans compared by a user.

3. The method of claim 1, wherein the first treatment plan has a first route for tooth movement comprising at least the first intermediate orthodontic appliance treatment stage and the second treatment plan has a second route for tooth movement comprising at least the second intermediate orthodontic appliance treatment stage, wherein the first and second routes are different.

4. The method of claim 1, wherein the first treatment plan has a first sequence of tooth movement comprising at least the first intermediate orthodontic appliance treatment stage and the second treatment plan has a second sequence of tooth movement comprising at least the second intermediate orthodontic appliance treatment stage, wherein the first and second sequences are different.

5. The method of claim 1, wherein the first treatment plan provides alignment of a first portion of the patient's arch and the second treatment plan provides alignment of a second portion of the patient's arch, wherein the first and second portions are different.

6. The method of claim 1, wherein the first treatment plan prescribes treatment using aligners formed of a first material and the second treatment plan prescribes treatment using aligners formed of a second material, wherein the first and second materials are different, and wherein the aligners formed of the first material and the aligners formed of the second material each comprise an orthodontic appliance having a geometry shaped to receive and reposition teeth from a position to a successive position.

7. The method of claim 1, wherein simultaneously displaying, with the treatment planning tool, includes superimposing a three-dimensional model of at least one of the first or second intermediate orthodontic appliance treatment stages over a three-dimensional model of the other of the first or second intermediate orthodontic appliance treatment stages from the different treatment plans.

8. The method of claim 1, wherein the at least one constraint comprises one or more of treatment cost, duration of treatment, number of aligners, or tooth movement routes.

9. The method of claim 1, wherein the at least one constraint comprises using interproximal reduction.

10. The method of claim 1, wherein the at least one constraint comprises a patient preference for a treatment completion date.

11. The method of claim 1, wherein the initial tooth data set is generated by scanning teeth of the patient.

12. The method of claim 1, further comprising:
manufacturing one or more of the different orthodontic appliances corresponding to the intermediate orthodontic appliance treatment stages of the treatment plan corresponding to the selected final orthodontic appliance treatment stage.

13. A method of orthodontic treatment planning with a comparative orthodontic treatment planning tool comprising a processor and memory, the method comprising:
receiving, at the treatment planning tool, an initial tooth data set comprising an initial tooth arrangement generating, by the treatment planning tool, a plurality of treatment plans to move teeth from the initial tooth arrangement based on the initial tooth data set, wherein:
  each of the plurality of treatment plans comprises a plurality of orthodontic appliance treatment stages including an initial orthodontic appliance treatment stage, a final orthodontic appliance treatment stage, and a plurality of intermediate orthodontic appliance treatment stages and is generated prior to displaying any of the plurality of intermediate orthodontic appliance treatment stages of the plurality of treatment plans to a dental practitioner,
  a first treatment plan of the plurality of treatment plans includes a first number of intermediate orthodontic appliance treatment stages,
  a second treatment plan of the plurality of treatment plans includes a second number of intermediate orthodontic appliance treatment stages different from the first number of intermediate orthodontic appliance treatment stages, and
  each of the plurality of intermediate orthodontic appliance treatment stages and each final orthodontic appliance treatment stage corresponds to a different orthodontic appliance;
receiving a user input, wherein the user input specifies at least one constraint for a desired orthodontic treatment plan;
providing at least two different treatment plans of the plurality of treatment plans, wherein both of the at least two different treatment plans meet the at least one constraint specified by the user input;
simultaneously displaying, with the treatment planning tool, three-dimensional models of tooth positioning of at least two different intermediate orthodontic appliance treatment stages from the at least two different treatment plans of the plurality of treatment plans on a screen for comparison by the dental practitioner, the at least two different intermediate orthodontic appliance treatment stages including a first intermediate orthodontic appliance treatment stage from the first treatment plan and a second intermediate orthodontic appliance treatment stage from the second treatment plan;
receiving, at the treatment planning tool, a selection of a final orthodontic appliance treatment stage based on the comparison of tooth positioning of the at least two different intermediate orthodontic appliance treatment stages and after displaying the at least two different intermediate orthodontic appliance treatment stages; and
manufacturing one or more of the different orthodontic appliances corresponding to the intermediate orthodontic appliance treatment stages of the treatment plan corresponding to the selected final orthodontic appliance treatment stage.

14. The method of claim 13, wherein the first treatment plan has a first route for tooth movement comprising at least the first intermediate orthodontic appliance treatment stage and the second treatment plan has a second route for tooth movement comprising at least the second intermediate orthodontic appliance treatment stage, wherein the first and second routes are different.

15. The method of claim 13, wherein the first treatment plan has a first sequence of tooth movement comprising at least the first intermediate orthodontic appliance treatment stage and the second treatment plan has a second sequence of tooth movement comprising at least the second intermediate orthodontic appliance treatment stage, wherein the first and second sequences are different.

16. The method of claim 13, wherein the first treatment plan provides alignment of a first portion of a patient's arch and the second treatment plan provides alignment of a second portion of the patient's arch, wherein the first and second portions are different.

17. The method of claim 13, wherein the first treatment plan prescribes treatment using aligners formed of a first material and the second treatment plan prescribes treatment using aligners formed of a second material, wherein the first and second materials are different, and wherein the aligners formed of the first material and the aligners formed of the second material each comprise an orthodontic appliance having a geometry shaped to receive and reposition teeth from a position to a successive position.

18. The method of claim 13, wherein simultaneously displaying, with the treatment planning tool, includes superimposing a three-dimensional model of at least one of the first or second intermediate orthodontic appliance treatment stages over a three-dimensional model of the other of the first or second intermediate orthodontic appliance treatment stages from the different treatment plans.

19. The method of claim 13, wherein the at least one constraint comprises one or more of treatment cost, duration of treatment, number of aligners, or tooth movement routes.

20. The method of claim 13, further comprising:
   administering, to a patient, one or more of the different orthodontic appliances corresponding to the intermediate orthodontic appliance treatment stages of the treatment plan corresponding to the selected final orthodontic appliance treatment stage.

* * * * *

UNITED STATES PATENT AND TRADEMARK OFFICE
CERTIFICATE OF CORRECTION

PATENT NO. : 11,850,111 B2
APPLICATION NO. : 14/695921
DATED : December 26, 2023
INVENTOR(S) : Mitra Derakhshan et al.

It is certified that error appears in the above-identified patent and that said Letters Patent is hereby corrected as shown below:

In the Claims

In Column 14, in Claim 1, Line 21, delete "tool" and insert -- tool, --.

In Column 15, in Claim 13, Line 67, delete "arrangement" and insert -- arrangement; --.

Signed and Sealed this
Sixth Day of February, 2024

Katherine Kelly Vidal
*Director of the United States Patent and Trademark Office*